United States Patent [19]

Steffler et al.

[11] Patent Number: 4,994,022
[45] Date of Patent: Feb. 19, 1991

[54] BLOOD CONSERVATION SYSTEM

[75] Inventors: Michael W. Steffler, Kalamazoo; Steven J. Carusillo, Portage, both of Mich.

[73] Assignee: Stryker Corporation, Kalamazoo, Mich.

[21] Appl. No.: 305,901

[22] Filed: Feb. 2, 1989

[51] Int. Cl.⁵ .................... A61M 5/00; A61M 37/00; A61M 1/00
[52] U.S. Cl. ....................................... 604/7; 604/317; 604/4; 604/5
[58] Field of Search ............... 604/4, 5, 6, 7, 119, 604/126, 317, 321

[56] References Cited

U.S. PATENT DOCUMENTS

| | | |
|---|---|---|
| 3,492,991 | 2/1970 | Dyer, Jr. . |
| 3,585,995 | 6/1971 | Perkins et al. . |
| 3,807,401 | 4/1974 | Riggle et al. . |
| 3,896,733 | 7/1975 | Rosenberg . |
| 3,933,150 | 1/1976 | Kaplan et al. . |
| 3,965,896 | 6/1976 | Swank . |
| 3,993,067 | 11/1976 | Schachet et al. . |
| 4,014,329 | 3/1977 | Welch et al. . |
| 4,424,053 | 1/1984 | Kurtz et al. . |
| 4,443,220 | 4/1984 | Hauer et al. . |
| 4,445,884 | 5/1984 | Kurtz et al. . |
| 4,500,308 | 2/1985 | Kurtz et al. . |
| 4,501,581 | 2/1985 | Kurtz et al. . |
| 4,540,406 | 9/1985 | Miles . |
| 4,540,413 | 9/1985 | Russo . |
| 4,547,186 | 10/1985 | Bartlett . |
| 4,551,131 | 11/1985 | Miles et al. . |
| 4,564,359 | 1/1986 | Rühland . |
| 4,569,674 | 2/1986 | Phillips et al. . |
| 4,631,050 | 12/1986 | Reed et al. . |
| 4,655,740 | 4/1987 | Rühland . |
| 4,655,754 | 4/1987 | Richmond et al. . |
| 4,664,682 | 5/1987 | Monzen ........................ 604/126 |
| 4,744,855 | 5/1988 | Rosenthal et al. . |
| 4,772,256 | 9/1988 | Lane et al. . |
| 4,775,360 | 10/1988 | Lane et al. . |
| 4,781,707 | 11/1988 | Boehringer et al. . |

*Primary Examiner*—Robert A. Hafer
*Assistant Examiner*—K. Owens
*Attorney, Agent, or Firm*—Flynn, Thiel, Boutell & Tanis

[57] ABSTRACT

A blood conservation system capable of receiving blood and lipids from a patient. A reservoir is releasably connectable to a patient for receiving body liquids, including blood. A transfusion unit is attached for receiving blood from the reservoir. The reservoir includes a valve unit actuable for transferring blood to the transfusion unit but preventing transfer of lipids. The valve unit also controls venting of the reservoir.

22 Claims, 4 Drawing Sheets

BLOOD CONSERVATION SYSTEM

FIELD OF THE INVENTION

This invention relates to a blood conservation system, and more particularly to a system for the collection, filtration and reinfusion of a patient's own blood or blood products, as a part of the treatment of vascular, cardiac, orthopedic, trauma, and the like patients.

BACKGROUND OF THE INVENTION

An absolutely safe and dependable homologous blood supply is currently unattainable. Proper technique can reduce the associated risks of homologous blood infusion, but complete safety is not yet attainable. Autotransfusion (the collection, filtration and reinfusion of the patient's own blood or blood products) is rapidly becoming an accepted adjunct in the treatment of vascular, cardiac, orthopedic and trauma patients. The American Medical Association, American Red Cross, and American Association of Blood Banks promote autologous blood transfusion as the "method of choice" in blood transfusion.

A known blood conservation system is marketed under the trade name "SULCOTRANS" by Sulco Basle, Inc. of Rockland, Md. This known system utilizes a rigid graduated collection reservoir and sterile single use drainage tube sets. However, reinfusion is direct from the collection reservoir. This prior art system collects liquid from the patient body by vacuum or gravity. However, the suction source is the conventional hospital wall suction outlet regulated to 80-100 mm. of mercury suction. Reinfusion is by gravity or handbulb attachment and a standard blood administration set can be used for reinfusion. The prior system uses a 260 micron pre-filter to clean liquid coming into the collection reservoir and uses a 40 micron post filter for liquid coming out of the collection reservoir and going toward the patient. The prior device is intended for use in post operative collection of surgical site drainage blood for auto-infusion.

U.S. Pat. Nos. 4,569,674 and 4,655,754 assigned to assignee of the present invention, disclose wound drainage apparatus usable during and after surgery, wherein a portable base unit includes a battery pack, a vacuum pump, and means for controlling operation of the vacuum pump. A portable reservoir is releasably insertable into the base unit. Upon insertion into the base unit, the reservoir is connected to the vacuum pump through a check valve and hydrophobic filter to prevent the vacuum pump from ingesting liquid from the reservoir. The reservoir in turn is connectable through a check valve to a draining wound on a patient. The vacuum pump responds to the physical presence of the reservoir in the base unit and to the gas pressure within the reservoir for maintaining the gas pressure in the reservoir at a desired range below atmospheric pressure. The reservoir is releasable from the base unit and, upon such release, maintains vacuum (sub-atmospheric pressure) therein. Thus, the reservoir, whether or not connected to the base unit, when at a sub-atmospheric pressure, can draw liquid from a wound. In one unit a flexible member atop the reservoir visually indicates the presence of a sub-atmospheric pressure in the reservoir by its physical shape (it dimples when the reservoir is at sub-atmospheric pressure).

The present inventors have recognized that the wound drainage system of above-mentioned U.S. Pat. Nos. 4,569,674 and 4,655,754 could desirably be adapted to, or form the basis for, a blood conservation system.

Accordingly, the objects and purposes of the invention include provision of the blood conservation system which is usable for receiving blood from a patient and for returning the blood or components thereof at some time thereafter to the patient, which is capable of separating lipids and the like from the patient's blood before returning it to the patient, which can draw liquid from a surgical site on a patient after a surgical procedure by suction and without need for connection to the conventional fixed suction sources incorporated in hospitals, which can be implemented with a liquid reservoir capable of connection to and disconnection from a portable base unit incorporating a battery source and vacuum pump, in which the reservoir can be at sub-atmospheric pressure for drawing liquid from the surgical site both when connected to the portable base unit and for a time following disconnection therefrom, and in which the reservoir is usable with a known and readily available portable base unit.

Further objects and purposes of the invention will be apparent to persons acquainted with apparatus of this general type upon reading the following description and inspecting the accompanying drawings.

SUMMARY OF THE INVENTION

A blood conservation system capable of receiving liquid, including blood, from a patient and comprising a reservoir connectable to the patient, transfusion means for receiving blood from the reservoir, and valve means for controlling the transfer of liquid from the reservoir.

DETAILED DESCRIPTION

A blood conservation system 10 (FIG. 1), embodying the invention, comprises a reservoir 11 releasably connectable to a portable base unit 12 for reducing the pressure within the reservoir to a sub-atmospheric pressure. The reservoir 11 is connectable to a surgical site (wound) not shown by a disposable tube set 13.

Figures 1, 2:
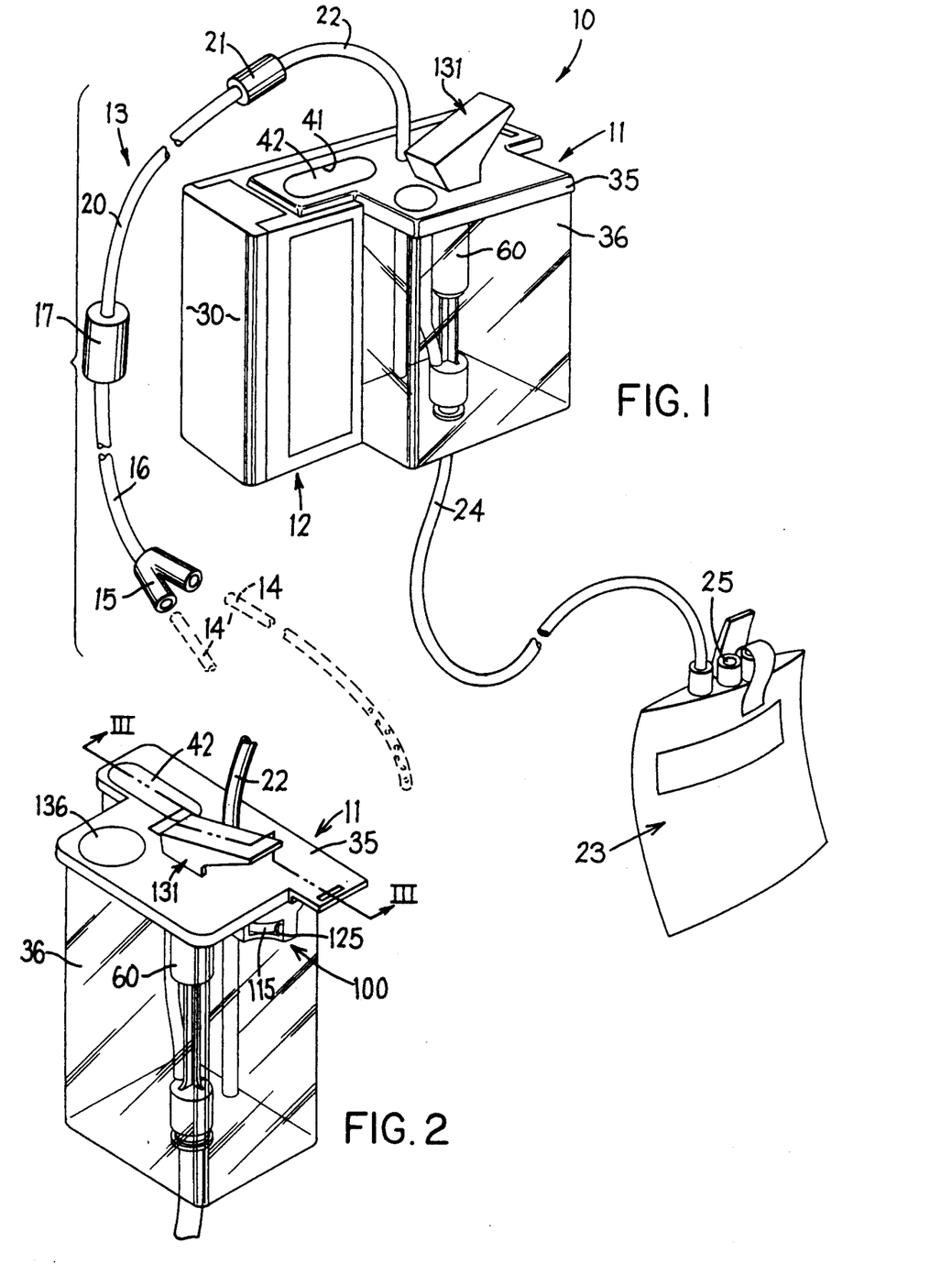
FIG. 1 is a fragmentary pictorial view of a blood conservation system embodying the invention.
FIG. 2 is a further pictorial view, taken from a different angle, of the reservoir of FIG. 1.

The tube set 13 comprises a drain tube, indicated in broken lines at 14, insertable in a conventional manner in a wound, usually at the time of surgery, to remove, by gravity or suction, liquid and other fluid materials to be drained from the wound, at the time of surgery and/or thereafter. Plural drain tubes (for example as at 14 and 14') may be joined by a Y-shaped fitting 15 to the remainder of the tube set 13 served by a single reservoir 11. The tube set 13 further comprises a first tube 16 connecting the Y-fitting to a prefilter 17. In the embodiment shown, the prefilter 16 is preferably a 160 to 260 micron prefilter provided for removal of bone chips, clotted blood and similar debris. A second tube 20 connects the prefilter 17 to an anti-reflux valve 21 (a check valve or one way valve, conveniently a so-called duckbill valve) oriented to permit liquid flow from the drain tube 14 to the reservoir 11 but prevent positively any reverse flow. A third tube 22 connects anti-reflux valve 21 to the top of the reservoir 11 for draining liquid from the drain tube 14 into the reservoir 11.

The blood conservation system 10 further includes a transfusion bag 23 connected by a fourth tube 24 to the bottom of the reservoir 11 for receiving blood therefrom. The transfusion bag 23 has at least one outlet 25 connectable in a conventional manner to a conventional blood administration set (not shown) for further handling of the blood therein, for example for immediate readministration to the patient, for processing in a conventional manner to readminister only certain components of the blood to the patient, for temporary storage prior to readministration to the patient, etc.

The drain tube 14, Y-fitting 15, tubes 16, 20 and 22, pre-filter 17, anti-reflux valve 21, tube 24, and transfusion bag 23 are all conventional parts which are readily and widely available commercially, and so are believed not to require further comment.

The base unit 12 may be of a kind commercially available from the assignee of the present invention. The internal structure and operation of an early version of the base unit 12 are disclosed in substantial detail in above-mentioned U.S. Pat. No. 4,569,674 assigned to the assignee of the present invention. A later version of the base unit 12, similar in configuration to that in present FIG. 1, is disclosed in later above-mentioned U.S. Pat. No. 4,655,754 (see particularly FIGS. 6 and 7), the relevant disclosures of both of the aforementioned patents being incorporated herein by reference.

Figure 3:
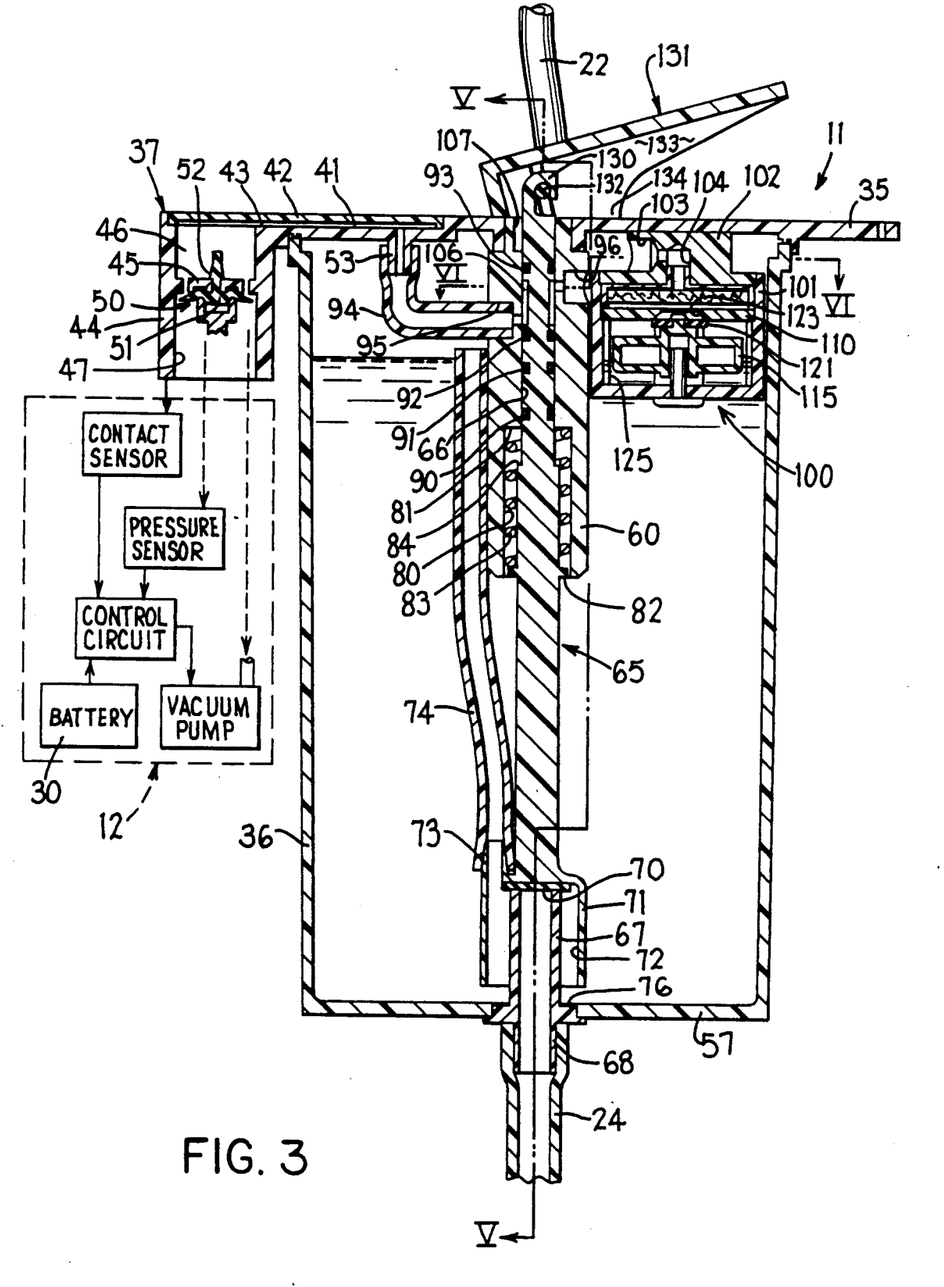
FIG. 3 is an enlarged, central cross-sectional view, taken substantially along the line III—III of FIGS. 2 and 6, and with the liquid outlet valve closed.

The portable base unit 12 (FIGS. 1 and 3) includes an electric supply in the form of an upwardly slidably removable, rechargeable, battery pack 30. As schematically indicated in FIG. 3, the base unit 12 further includes a vacuum pump and a control circuit. The control circuit turns on the vacuum when a contact sensor signals that a reservoir (here for example the reservoir 11) has been downwardly inserted into the base unit 12 and a pressure sensor signals simultaneously that the pressure in the reservoir is above the desired sub-atmospheric range. Both conditions are needed to turn on the vacuum pump. The vacuum pump is off when no reservoir 11 is plugged into the base unit 12. The vacuum pump is also off when the reservoir 11 plugged into the base unit 12 is at a sub-atmospheric pressure in the desired preset range. The desired preset range may for example occupy a portion of the range between atmospheric pressure and at least 2.4 PSI below atmospheric pressure, which is within the range of capability of the vacuum pump in one form of the base unit 12.

Aforementioned U.S. Pat. No. 4,655,754 discloses a reservoir usable with the base unit 12 of present FIG. 1 and adapted for wound drainage but not for use in a blood conservation (e.g. auto-transfusion) system. The drain reservoir 11 of the present application, as can be seen from FIG. 3 for example, may be similar to the drain reservoir of aforementioned U.S. Pat. No. 4,655,754 to the extent of having a cover 35 (FIG. 3) cantilevered at 36 beyond the left end of the upward opening bottle 36 of the reservoir 11. To adapt the present reservoir 11 to use with the base unit 12 above described, the leftward portion of the cover 35, including the leftward, overhanging portion 37 may be structured much like that of the corresponding portion of the reservoir in aforementioned U.S. Pat. No. 4,655,754. Thus, in present FIG. 3, the leftward portion of the cover 35 has an upward opening recess 41 (FIG. 3) which extends from the central portion of the cover 35 nearly to the left end 37 thereof. A plate-like enclosure 42 is sealingly fixed in the recess 41 to close the top thereof. A vacuum, or suction, passage 43 is formed by the recess 41 and plate-like closure 42. A leg 44 integrally depends from the left end of the cover 35 in close spaced relation to the left side of the bottle 36. Approximately midway down the leg 44, a wall 45 extends laterally within the leg to separate the hollow interior of the leg 44 into an upper chamber 46 communicating with the vacuum passage 43 thereabove, and a downwardly opening recess 47 communicable with the pressure sensor and vacuum pump in the base unit 12.

A check, or one way, valve 50 here comprises a conventional resilient umbrella valve head 51 depending from a coaxial stem 52 fixed in a central opening in the overlying wall 45, the stem 52 being enlarged adjacent its free end to firmly hold the radially enlarged head 51 normally in sealing contact against the wall 45. The valve 50 may for example be a Part No. VA 3123, available from Vernay, Inc., of Yellow Springs, Ohio. Holes through the wall 45 are closed by the overlapping umbrella valve head 51 when the air pressure in the recess 47 is higher than that in the upper chamber 46, i.e , when there is a sub-atmospheric pressure in the bottle 36. On the other hand, the valve head 51 is capable of opening by deflecting downward at its periphery for drawing air from the bottle 36 through the vacuum passage 43 and past the check valve 50 into the vacuum pump in the base unit 12. If desired, the opening of the umbrella valve 50 may be merely in response to an above-limit pressure in the reservoir 11. Alternately, it is contemplated that the valve 50 can be mechanically opened by insertion of the reservoir 11 into the base unit 12. For example, upward bending of a radially intermediate portion of the umbrella valve head 51 into a downward facing annular groove in the bottom of the wall 45 (radially closely surrounding the stem 52), by a fork-like prod 49, fixed on and upstanding from the base unit 12, bends the periphery of the head 51 down away from the wall 45 to open the holes in the wall 45.

The reservoir 11, embodying the present invention, departs from the reservoir of aforementioned U.S. Pat. No. 4,635,754 as hereafter described.

The vacuum passage 43, in the embodiment of the present invention shown in present FIG. 3, communicates with a nipple 53 which depends from the cover 35 into the interior of the bottle 36, for purposes appearing hereinafter.

The reservoir 11 is substantially greater in fore/aft thickness (right to left in FIG. 5) than the drainage reservoir of aforementioned U.S. Pat. No. 4,635,654. The greater fore/aft thickness provides additional volume for greater liquid storage and provides room for the additional internal structure of the reservoir 11 hereafter discussed.

Figure 4:
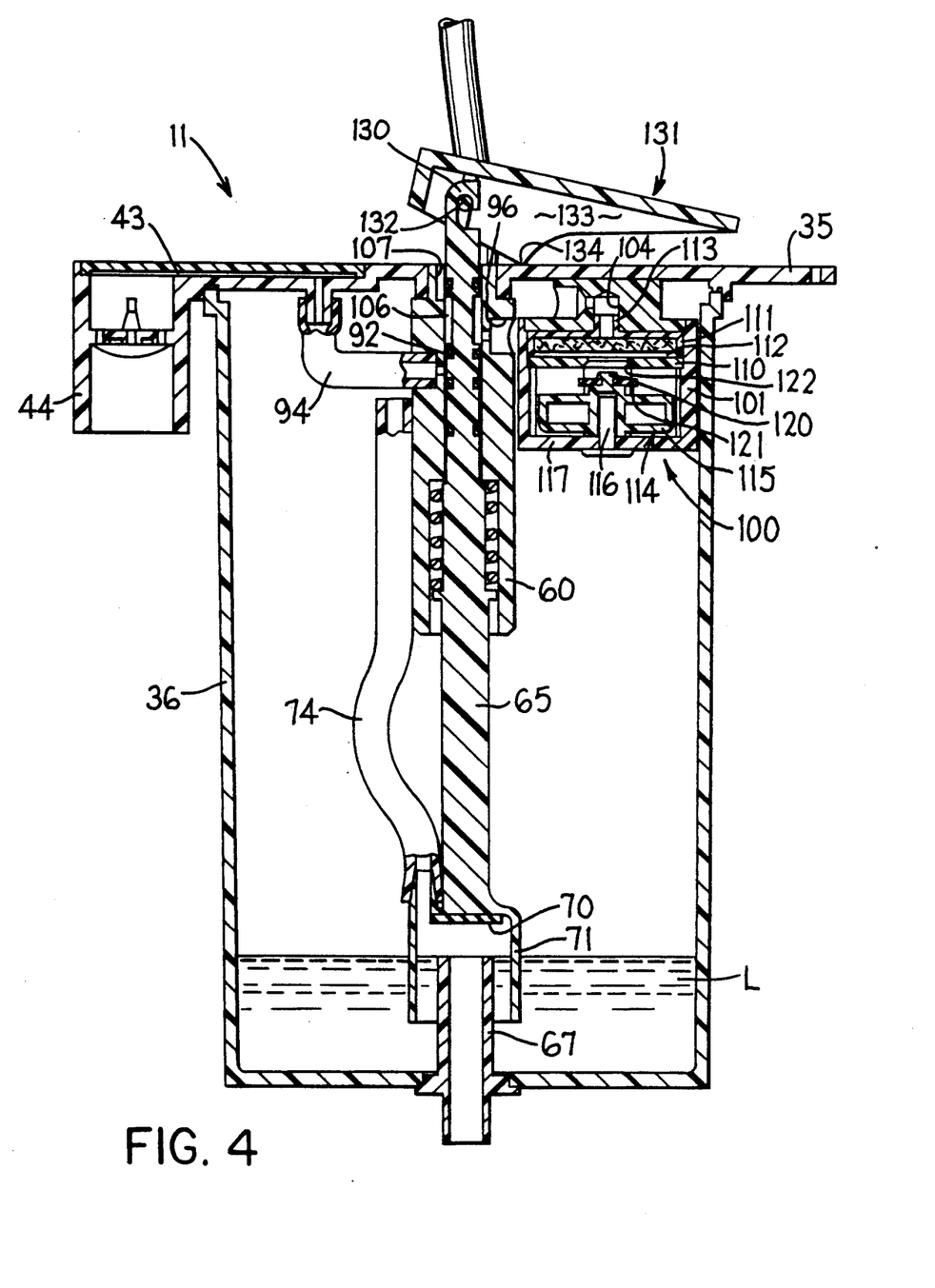
FIG. 4 is a view similar to FIG. 3 but with the outlet valve open.
Figure 5:
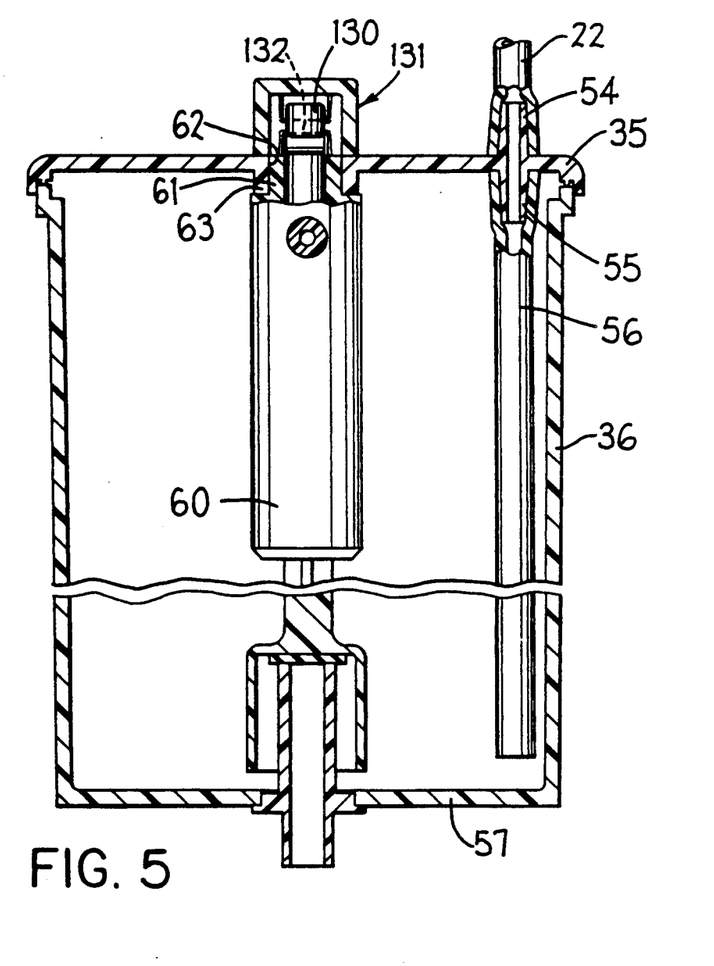
FIG. 5 is a view substantially taken along the line V—V of FIG. 3 and particularly showing the liquid inlet line to the reservoir.
Figure 6:
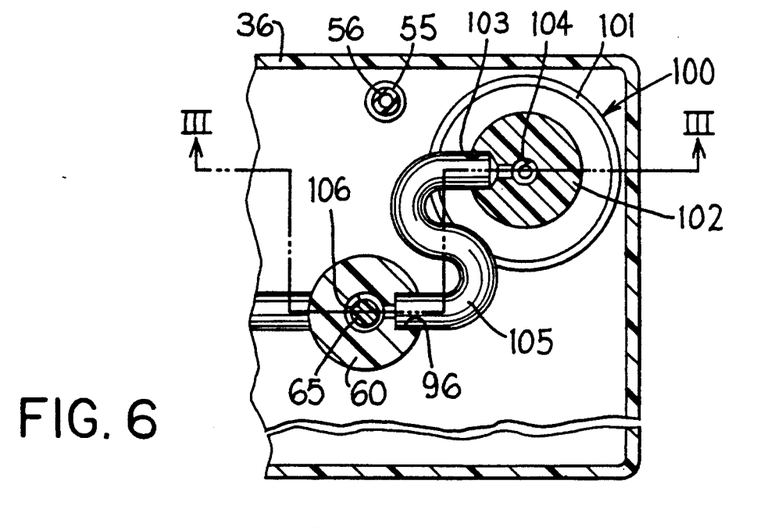
FIG. 6 is a sectional view substantially taken on the line VI—VI of FIG. 3 and showing the vent/suction passage from the valve stem to the top of the hydrophobic filter of FIG. 3.

Along its rearward (rightward in FIG. 5) edge and generally centrally of the bottle 36, as seen from right to left in FIGS. 3, 4 and 6, the cover 35 is provided with coaxial, communicating, upstanding and depending nipples 54 and 55 (FIG. 5). The outlet end of the tube 22 of the drainage tube set 13 is sealingly sleeved over the upstanding nipple 54 and thereby communicates with a liquid inlet tube 56 which is sealingly sleeved over the depending nipple 55. The inlet tube 56 depends downward into the bottle 36 to within about one-quarter inch of the bottom wall 57 of the bottle 36. Blood and other fluid material drawn into the bottle 36 through the tube set 13 and liquid inlet tube 56, exits from the bottom of the latter to progressively fill the bottle 36. Location of the outlet end of the liquid inlet tube 56 near the bottom wall 57 of the bottle 36 reduces splashing of the incoming blood and other liquid and reduces the possibility of physical injury to the incoming blood cells due to violent collision with each other or with the hard internal surfaces of the bottle 36.

A tubular valve guide 60 (FIG. 3) is fixed to and depends vertically from the cover 35 and substantially centrally down into the interior of the bottle 36. In the embodiment shown, the valve guide 60 is somewhat less than about one-half the vertical height of the bottle 36. The top end portion 61 of the guide 60 is stepped to a reduced diameter and received through a snug opening 62 in the cover 35 where it is fixedly secured, by any convenient means such as a suitable adhesive. To firmly fix the depending guide 60 with respect to the cover, the cover is provided with a depending annular flange 63 which receives and fixedly supports the stepped top end portion 61 of the guide 60.

A tubular standpipe 67 extends in a fixed, sealed manner centrally through the bottom wall 57 of the bottle 36. The standpipe 67 is preferably centered on the bottom wall 57. The tube 24 of FIG. 1 is sealingly sleeved over a nipple 68 depending from the bottle bottom wall 57 and defining the lower end of the standpipe 67. The standpipe 67 extends from the bottle floor 57 upward to a height above the floor 57 (in the embodiment shown about an inch) which will exceed the likely thickness of a layer of unwanted fatty materials, such as lipids, which may enter the reservoir 11 with blood from the wound and tend to form a layer floating on top of the blood.

A vertically elongate valve stem 65 is vertically slidably supported in a longitudinal, central, through bore 66 of the tubular valve guide 60. The guide 60 and valve stem 65 are coaxially aligned above the standpipe 67. Fixed to the bottom end of the stem 65 is a flat, resilient valve disk 70 which, in the lower position of the valve stem 65 shown in FIG. 3, seats upon and closes the open top of the standpipe 67. Fixed to the bottom of the stem 65 is a depending hood 71. The hood 71 defines a downwardly opening recess 72 of diameter somewhat exceeding the diameter of the standpipe 67, for radially loosely receiving the standpipe 67 therein. In FIG. 3, the hood 71 extends downward from the valve disk 70 to within a short distance, for example a quarter inch, from the bottom wall 57 of the reservoir 11. Thus, the hood 71 is somewhat shorter vertically than the standpipe 67.

At one side of the stem 75, the hood 71 is provided with an upstanding nipple 73, which extends above the level of the valve disk 70. The lower end of a flexible gas vent tube 74 sealingly sleeves over the nipple 73. The gas vent tube 74 extends upward from the hood 71 and is fixed, by any convenient means not shown (such as an adhesive or a clamp) to the side of the guide 60. The upper end of the gas vent 74 opens upward near, but spaced slightly downward from the underside of the cover 35, for example about three quarters of an inch therebelow. The top of the tube 74 is above the level to which liquid is allowed to rise in the bottle 36.

Raising of the valve stem 65, from its FIG. 3 position to its elevated FIG. 4, position lifts the valve disk 70 from the top of the standpipe 67 and thus permits communication between the standpipe 67 and the interior of the bottle 36, past the bottom of hood 71. To accommodate the upward displacement of the stem 65, the gas vent tube 74 flexes laterally as indicated in FIG. 4.

Even in the uppermost position of the valve stem 65, shown in FIG. 4, the hood 71 still extends below the top of the standpipe 67. Thus, a layer of unwanted lipids and the like, floating atop the blood in the reservoir, is blocked by the depending hood 71 from access to the open top of the standpipe 67 and therefore cannot escape from the reservoir 11 into the tube 24 leading to the transfusion bag 23. Thus, floating contaminants, such as lipids, are prevented from passing from the reservoir 11 to the transfusion bag 23 (FIG. 1), but the heavier blood in the reservoir 11 is allowed to pass under the hood 71 (FIG. 4) and down into the open top of the standpipe 67 and thence through the tube 24 into the transfusion bag 23, at least until the level of liquid in the reservoir 11 drops to a level even with the top of the standpipe 67.

Where liquid drains from the reservoir by gravity (as it would in FIG. 1, for example, where the transfusion bag 23 is located below the level of the reservoir 11) the gas vent tube 74 vents the upper end of the hood 71 to the top portion of the interior of the bottle 36 so that the pressure in these two locations is the same. Accordingly, liquid passing from the bottle 36 downward through the standpipe 67 and tube 24 into the transfusion bag 23 cannot itself drop the pressure within the hood 71 to less than the pressure within the bottle 36, and so cannot itself suck liquid from the bottle 36 and thereby cause the minimum liquid level in the bottle 36 to drop below the top of the standpipe 67. Thus, the vent tube 74 prevents sucking of any part of the floating layer of lipids or other unwanted materials under the hood 71 and down through the standpipe 67. Thus, the standpipe 67, hood 71 and gas vent tube 74 act in concert to prevent unwanted floating materials, particularly lipids, to be drawn with the blood from the reservoir 11 into the transfusion bag 23, when the valve 70 is opened by lifting of the stem 65 to its upper FIG. 4 position.

A downward opening recess 80 in the valve guide 60 is coaxial with and enlarges the diameter of the bottom portion of the bore 66. The recess 80 forms a downward facing step 81 in the bore 66. A radially outwardly extending flange 82 is fixed on the valve stem 65 intermediate the ends thereof. The flange 82 is of sufficiently small diameter to be freely slidable within the recess 80 in the valve guide 60. The diameter of the stem 65 above the flange 82 is less in diameter than the recess 80, and a spiral compression spring 83 is axially freely slidably disposed in the elongate annular space between the periphery of the stem 65 and the inner peripheral wall of the recess 80. The spring 83 is axially trapped between the flange 82 on the stem 65 and the downward facing step 81 of the valve guide 60. Thus, the spring 83 resiliently urges the valve stem 65 downward with respect to the valve guide 60 and overlying cover 35, so as to urge the valve disk 70 firmly against the top of the standpipe 67 to seal the latter against escape of liquid from the reservoir 11.

The valve stem 65 has an upward facing step 84 opposed to the downward facing step 81 in the valve guide 60. In the lower position of the stem 65, shown in FIG. 3, the steps 81 and 84 are spaced vertically by a distance substantially less than the height of the hood 71. Thus, the valve stem 65 can move upward only to a limited extent, until the two steps 81 and 84 collide, at which position the hood 71 still substantially vertically overlaps the standpipe 67, as seen in FIG. 4.

The reduced diameter, upper portion of the stem 65, above the step 84 thereof, cooperates with and is snugly vertically slidable in the portion of the through bore 66 above the recess 80, for providing further valve functions as hereafter discussed. These functions include, in the FIG. 3, downward position of the valve stem 65, connecting the upper portion of the interior of the bottle 36 to the suction leg 44 to draw gases from and thereby reduce the pressure in the bottle 36 to subatmospheric pressure. Alternately, with the valve stem 65 in its FIG. 4, upper position, these valve functions include disconnecting the interior of the bottle 36 from the suction leg 44 and instead opening the interior of the bottle 36 to the atmosphere above the cover 35 to permit drainage of liquid in the bottle 36 through the standpipe 67.

To accomplish these valving functions, annular seals 90, 91, 92 and 93 (FIG. 3) are spaced along the valve stem 65 and seal against the reduced diameter upper portion of the through bore 66 above the step 81. In the embodiment shown, the annular seals 90-93 are conveniently resilient O rings received in corresponding annular grooves spaced along the length of the reduced diameter upper portion of the valve stem 65.

As seen in FIG. 3, a flexible tube 94 sleeves over the suction nipple 53 and at its other end is fixed in a recessed hole 95 communicating through the sidewall of the valve guide 60, to open into the through bore 66 in spaced relation vertically between the spring recess 80 and the cover 35.

The ends of the tube 94 are sealingly fixed over the nipple 53 and in the recessed hole 95 to communicate the vacuum passage 43 with the through bore 66 of the tubular valve guide 60.

A further recessed hole 96 (FIGS. 3 and 6) communicates with the bore 66 of the valve guide 60 at a location spaced axially between the hole 95 and the cover 35. In the embodiment shown, the hole 96 extends laterally away from the hole 95.

Spaced to the right and rear of the tubular valve guide 60, and depending from the underside of the cover 35, is a protective unit 100 (FIG. 4) comprising a generally circular casing 101. The casing 101 is covered by a reduced diameter upper end portion 102 (FIGS. 3 and 6) fixed by any convenient means, such as adhesive bonding, to the underside of the cover 35. A recessed hole 103 in the upper end portion 102 communicates with a central opening 104 in the casing 101. The recessed hole 103, in the embodiment shown, faces generally leftward. A flexible tube 105 (FIG. 6) has opposite ends sealingly fixed in the recessed holes 96 and 103 respectively, the tube 105 extending generally in a S-shape therebetween.

Returning to the valve stem 65, the topmost O-rings 92 and 93 are spaced axially along the stem 65 at opposite ends of an axially elongate annular groove 106 in the stem. With the stem 65 in its normal downward position of FIG. 3, the annular groove 106 communicates the recessed holes 95 and 96 in the valve guide 60 and thereby connects the suction leg 44 to the vacuum passage 43 and tube 94 through the recessed hole 96, tube 105 (FIG. 6) and central opening 104 in the upper end portion 102 of the protective unit 100.

An axial depression 107 (FIG. 3) in the interior surface of the bore 66 extends from a point just above the upper O-ring 93, with the latter in its downward position of FIG. 3, upward along the periphery of the upper end portion of the stem 65, to open through the top surface of the cover 35 to the atmosphere surrounding the reservoir 11. In the lower, FIG. 3 position of the stem 65, the upper O-ring 93 prevents venting of the reservoir 11 to the atmosphere. On the other hand, in the upper position of the valve stem 65 shown in FIG. 4, the upper O-ring 93 is lifted above the bottom of the axial depression 107 to communicate the atmosphere surrounding the reservoir 11 through the axial depression 107, annular groove 106, the recessed hole 96, the tube 105 (FIG. 6), the central opening 104 in the upper end portion 102 of the protective unit 100, with the interior of the bottle 36.

The lower O-rings 90 and 91 are, in both the upper and lower positions of the stem 65, located below the tube 94 and thus provide a redundant seal to insure that liquid within the bottle 36 cannot reach the vacuum passage 43 and suction leg 44 by seeping between the valve stem 65 and valve guide 60. Also, the lowermost O-ring 90 is spaced below the adjacent O-ring 91 by a distance greater than the stroke length of the valve stem 65. Thus, there is a short vertical segment of the valve guide bore 66, between the O-rings 90 and 91, that neither of the O-rings 90 and 91 can contact. This prevents possible contaminants from entering the reservoir 11 through the air vent 107 and passing down the bore 66 into contact with liquid in the bottle 36.

The protective unit 100 (FIGS. 2 and 4) has a washer-like, horizontally extending divider 110 (FIG. 4) which separates the hollow interior of the casing 101 into upper and lower chambers. The upper chamber contains a conventional hydrophobic filter 111 (for example of the kind shown in the above-referenced U.S. Pat. No. 4,655,754) which substantially fully occupies the upper chamber except for a vertically thin space 112 immediately above the divider 110. The hydrophobic filter has a central, upstanding nipple 113 snugly and sealingly received in the bottom portion of the central opening 104. The hydrophobic filter 111 permits a suction source, connected to the depending suction leg 44, to draw air and other gases from the interior of the bottle 36 upward therethrough (with the valve stem 65 in its normal lowered position FIG. 3) but prevents liquid from passing therethrough. On the other hand, with the valve stem 65 in its raised FIG. 4 position, the very small pore size (for example about 2 microns) of the pores in the hydrophobic filter 111 are small enough to in effect sterilize ambient air drawn from the atmosphere, through the axial depression 107 and thus eventually downward through the hydrophobic filter 112 into the bottle 36. This prevents airborne bacteria and the like from entering the bottle 36 and contacting, and possibly contaminating, blood therein.

Below the annular divider 110, a casing 101 has a lower chamber which is loosely occupied by a float valve 114. In the embodiment shown, the float valve 114 comprises an annular float 115 loosely disposed in the lower chamber for rising and falling therein. A stub shaft 116 is fixed to and extends up through the bottom 117 of the protective unit casing 101. The float 115 has a downwardly opening central recess in which the stub shaft 116 is snugly but axially slidably located, to positively guide the rise and fall of the float 115. Extending upward from the float 115 is a central peg 120 which fixedly supports a resilient, washer shaped valve member 121. The cup shaped casing 101 has openings 125 in the side wall thereof for admitting liquid into contact with the float 115, so that the float rises and falls in response to corresponding changes in liquid level in the bottle 36.

With the liquid in the bottle 36 below a desired maximum level, the float 115 is not lifted by such liquid but rather remains at or near its lowermost position shown in FIG. 4. In this way, the valve means 121 are not lifted into contact with the central opening (valve seat) 122.

On the other hand, when the liquid level in the bottle 36 rises to a sufficient level, to float the float 115 (as seen in FIG. 3), the float 115 rises until the annular valve member 121 rises up into contact with the downwardly flared valve seat 123 in the washer-like divider 110, to close and seal the valve seat 123 and thereby isolate the interior of the bottle 36 both from the atmosphere 107 and from the vacuum passage 43 and suction leg 44.

Fixed atop the stem 65 and protruding upward through the cover 35 is a hook 130 by means of which the stem 65 can be raised and lowered between its FIGS. 3 and 4 positions. To facilitate raising and lowering of the valve stem 65, an inverted L-shaped cross section handle 131 (FIGS. 3 and 4) has a cross shaft 132 over which the hook 130 is hooked. The handle 131 has depending side walls 133. The side walls 133 at their lower right corner define a fulcrum 134 about which the handle 131 is pivotable, by depressing and raising the rightward end of such handle.

A flexible disk 136 (FIG. 2) is fixed in an opening in the cover 35 and visibly flexes, to change contour (dimples) in response to application of sub-atmospheric pressure to the interior of the bottle 36, so that a person can, by inspecting the shape of the disk 136, tell whether there is a sub-atmospheric pressure in the bottle 36.

The apparatus may be constructed of any desired material. In one embodiment constructed according to the invention, and by way of example, the flexible tubes were of PVC, and the rigid parts of the reservoir were of molded plastics material, for example polycarbonate.

OPERATION

The reservoir 11 can be assembled as follows. The protective unit 100 preferably is assembled by upwardly inserting the stub shaft 116 through a snug central opening in the bottom of the upwardly opening, cup shaped casing 101, whereupon the float 115 (with attached resilient valve washer 121) is dropped into the casing 101 to loosely sleeve over the upper end of the stub shaft 116, so as to be free to rise and fall with changes in liquid level.

The washer-like horizontal divider 110 is then fixed within the cup shaped casing 101 (for example by seating upon an unnumbered, narrow, upward facing step shown in FIG. 3). The hydrophobic filter 111 has its upstanding central nipple 113 plugged into the central opening 104 in the upper end portion 102. The upper end portion 102, with the underlying hydrophobic filter 111, is then plugged into the open top of the casing 101. The parts fixed together as above described are held together by any convenient means, such as adhesive bonding. The top of the upper end portion 102 of protective unit 100 is secured, as by adhesive bonding, to the underside of the cover 35.

The valve guide 60 is pendently fixed to the underside of the cover 35 by upward insertion of its top end portion 61 snugly and fixedly into the central hole 62 in the cover 35. The spring 83 is slid down over the top portion of the valve stem 65 and the latter, with the valve disk 70 fixed, as by adhesive bonding, to the bottom thereof, is upwardly inserted into the valve guide 60 so that its hooked upper end 130 protrudes out above the top cover 35. The O rings 90-93 are preassembled on the upper portion of the stem 65 in the manner shown in the drawings With the handle 131 sitting atop the cover 35 slightly to the right of its position of FIG. 3, the valve stem 65 is manually pushed up as far as possible in the valve guide 60. The handle 131 is then slid leftward to side the shaft 132 therein under the hook 130 at the upper end of the valve stem 65. The valve stem 65 is then allowed to drop, so that the hook 130 drops over and captures the shaft 132 of the handle 131. Thus, the valve stem and handle are connected releasably in the manner shown in FIGS. 3 and 4.

The tube 105 (FIG. 6) then has its ends inserted into the recessed holes 96 and 103 in a fixed, sealed manner. The tube 94 can then similarly be snugly and fixedly sleeved over the nipple 53 and snugly and fixedly inserted into the recessed hole 95 in the valve guide 60. The gas vent tube 74 can then similarly be fixedly and snugly sleeved over the nipple 73 and fixedly secured near its upper end to the side of the valve guide 60.

The above-mentioned fixed connections between the valve guide 60 and tubes 74, 94 and 105 can be secured, as by adhesive bonding, as can be the securement of the tube 94 to the nipple 53.

The umbrella shaped check valve 50 can at this point be upwardly inserted through the central opening of the wall 45 within the hollow suction leg 44. The plate-like closure 42 can be fixed to cover the flat recess 41 in the cover 35 by adhesive bonding along its edges.

The liquid inlet tube 56 can, at its upper end, be sleeved over the depending nipple 55, and if desired, secured thereto by adhesive bonding. Also, the standpipe 67 can be inserted upward through the central opening 76 in the bottom 57 of the bottle 36. The standpipe 67 here has a radially outwardly extending flange spaced intermediate its ends, which flange is fixedly received in the opening 76 and may be secured thereto by adhesive bonding.

At this point, the cover 35, carrying the above-named parts fixed thereto, can be placed atop the bottle 36 with the valve stem 65 coaxially aligned above the standpipe 67. The cover 35 can then be fixed to the top of the bottle 36 by any convenient means, such as adhesive bonding. This completes assembly of the reservoir 11

To ready the reservoir 11 for collecting blood, a tube set 13 is secured thereto. More particularly, the tube 22 of the tube set is snugly and sealingly sleeved over the upstanding nipple 54 atop the cover 35. The drain tube 14 (or 14 and 14' if a Y fitting 15 is provided) can then be inserted into a wound to be drained. The inlet tube 24 of the transfusion bag 23 is intended to be permanently sealingly sleeved over the downwardly protruding nipple 68 on the underside of the bottle 36, as shown in FIG. 1.

With a charged battery 30 inserted into the base unit 12 (FIG. 1), the reservoir 11 can be downwardly inserted into the base unit in the manner shown in above-mentioned U.S. Pat. No. 4,655,754. If the gas pressure in the reservoir 11 is not in its preset sub-atmospheric pressure operating range, the vacuum pump in the base unit 12 turns on. With the valve stem 65 in its lower, FIG. 3 position, the vacuum pump in the base unit 12 draws gases (normally air) from the interior of the bottle 36 through the openings 125 in the protective casing 101, up past the open valve seat 123, through the hydrophobic filter 111, central opening 104, recessed hole 103, tube 105 (FIG. 6), recessed hole 96, annular groove 106, tube 94, vacuum passage 43, and the check valve in the suction leg 44 and thence to the base unit 12 and its vacuum pump. In this downward position of the valve stem 65 shown in FIG. 3, the valve stem 65 shuts off any communication of bottle 36 with the axial depression 107 (the vent to the atmosphere) and standpipe 67. Thus, the base unit 12 can reduce the pressure within the bottle 36 to a sub-atmospheric pressure in a desired range. A typical sub-atmospheric pressure range to which the base unit 12 can be set is, for example, 0.5 PSI to 2.4 PSI below atmospheric pressure.

The sub-atmospheric pressure in the bottle 36 draws blood, and in many instances some unwanted flowable materials such as lipids or other fatty substances, from the wound, through the tube set 13 (FIG. 1) toward the reservoir 11. As above described, the pre-filter 17 acts to remove solid particles such as bone chips and the like from the flow.

Although the base unit 12 is portable, it may be desired to remove the reservoir 11 from the base unit, since the reservoir 11 is lighter, more compact and hence even more portable when not attached to the base unit 12. After release from the base unit 12, the sub-atmospheric pressure in the reservoir 11 is preserved against loss by automatic closure of the check valve 50, so that the reservoir can continue to draw fluid from the wound through the tube set 13.

As a result, the level of liquid in the reservoir begins to rise. The entering liquid rises past the top of the hood 71 (FIG. 3). The vent tube 74 allows the liquid to rise within the hood 71 as it rises outside the hood.

As above stated, the hydrophobic filter 111 permits gases, such as air, to be withdrawn from the bottle 36 the base unit 12, but blocks liquids from passing therethrough. Thus, if liquid enters the protective unit 100, due to splashing, tilting of the reservoir, normal rise, or any other reason, and the float valve 121, 123 should unexpectedly fail to close, the hydrophobic filter 111 prevents contamination of the vacuum pump in the base unit 12.

Should the liquid rise enough, it will contact and lift the float 115 until the rising float 115 pushes the annular valve means 121 against the valve seat 123 to close the float valve and thus prevent any further exit of gases and liquid upward to the hydrophobic filter 111. Once the float valve 121, 123 is closed, and assuming the reservoir 11 is plugged into the base unit 12, the central opening 104, holes 103 and 96, tube 94, vacuum passage 43, and suction leg 44 rapidly drop in pressure, until below the desired, preset range and this shuts off the vacuum pump in the base unit 12, in the manner discussed in the aforementioned U.S. Pat. No. 4,655,754. At the same time, the closed float valve 121, 123 and high liquid level prevent any significant additional amount of liquid from being drawn into the reservoir 11.

Liquid, particularly blood, can be emptied from the bottle 36 when desired. For example, blood in the bottle 36 can be emptied through the tube 24 into a transfusion bag 23 as follows. The handle 131 is depressed from its FIG. 3 to its FIG. 4 position, by the hand of the operator, to lift the valve stem 65 with respect to the valve guide 60. As seen in FIG. 4, this has several effects.

First, the vacuum path through the tube 94 is cut off from the recessed hole 96 by the correspondingly raised 0 ring 92. Thus, after the liquid level within the bottle 36 falls sufficiently (as hereafter discussed) and the float 115 falls and opens the float valve 121, 123, the interior of the bottle 36 remains disconnected from the vacuum passage 43.

Second, the valve disk 70 is lifted off the top of the standpipe 67. The heavier liquids, such as blood, pass under the bottom of the hood 71 and over the top of the standpipe 67 to exit through the tube 24. Lighter liquids, such as lipids and the like, float in a more or less discreet layer atop the blood. Blood continues to drain from the reservoir 11 until the top of the liquid mass lies about level with the top of the standpipe 67, as shown in FIG. 4. Then no more liquid flows out of the reservoir 11, such that the layer of unwanted floating material (lipids and the like) when its top is flush with the top of the standpipe 67, its bottom does not extend downward to the bottom of the hood 71, so that no appreciable portion of this unwanted floating material layer L can escape from the bottle 36 and enter the transfusion bag 23, thus keeping the transfusion bag 23 free of it. The venting of the top of the hood 71 by the flexible tube 74 keeps the gas pressure under the hood 71 equal to that in the rest of the bottle 36. Thus, the pull of gravity downward on the liquid within the exit tube 54 cannot stuck, or siphon, the unwanted floating lipids layer L down under the bottom of the hood 71, up into the hood 71 and then down through the standpipe 67.

As a result, the aforementioned apparatus permits removal of the blood (or most of it) from the bottle 36 into the transfusion bag 23 for subsequent transfusion back to the patient, while eliminating the unwanted lipids.

Third, the valve stem 65 in its upward position of FIG. 4 vents the interior of the bottle 36 past the float valve 121, 123, hydrophobic filter 111, holes 103 and 96, thence through the annular groove 106 and axial depression 107 to the atmosphere surrounding the reservoir 111. Such venting permits the aforementioned drainage of the bottle 36 through the standpipe 67.

When the bottle 36 has been sufficiently drained of liquid, the operator can then pivot the handle 131 counterclockwise back to its rest position at FIG. 3, thus allowing the spring 83 to return the valve stem 65 to its downward position of FIG. 3, thereby closing the top of the standpipe 67 and the passage through the axial vent depression 107 and restoring the connection of the vacuum passage 43 through the hydrophobic filter and float valve into the bottle 36 to once again enable production of the pressure in the bottle 36 to the desired atmospheric range.

During venting of the upper portion of the bottle 36 to the atmosphere as seen in FIG. 4, the hydrophobic filter 111, due to its very small effective pore size, for example an effective pore size of one micron or less for example 0.45 microns, acts to sterilize the incoming air entering the bottle 36 by mechanically blocking entry of bacterial agents and the like.

The tubes 14, 16, 20, 22, 24 and 56 are preferably of a flexible resilient material such as PVC.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A blood conservation system capable of receiving blood and lipids from a patient, the system comprising:
   a reservoir;
   means for releasably connecting said reservoir to a patient for receiving body liquids including blood from the patient;
   transfusion means for receiving blood from said reservoir; and
   means for transferring blood from said reservoir to said transfusion means but preventing transfer of lipids from said reservoir to said transfusion means, said transfusion means comprising a standpipe located within the bottom portion of the reservoir and opening at a level spaced above the bottom of the reservoir for receiving liquid from the reservoir, and a hood loosely telescoped over the standpipe, the hood and standpipe having a respective outflow position permitting flow of liquid therebetween from the reservoir down through the standpipe while preventing a predetermined thickness top layer of liquid in the reservoir from escaping past the hood to the standpipe, such that lipids and other unwanted materials trapped in such top layer cannot enter the standpipe whereas blood underlying said top layer can enter said standpipe.

2. The apparatus of claim 1 in which said hood is an inverted cup-shaped hood loosely telescoped over said standpipe, and defining valve means actuable for opening and closing said standpipe opening.

3. A blood conservation system capable of receiving blood and lipids from a patient, the system comprising:
   a reservoir;
   means for releasably connecting said reservoir to a patient for receiving body liquids including blood from the patient;
   transfusion means for receiving blood from said reservoir; and
   means for transferring blood from said reservoir to said transfusion means but preventing transfer of lipids from said reservoir to said transfusion means, said transfusion means comprising a standpipe opening at a level spaced above the bottom of said reservoir for receiving liquid from the reservoir, in inverted cup-shaped hood loosely telescoped over the standpipe, and valve means for opening and closing said standpipe opening, in which said standpipe extends up from the floor of said reservoir, said valve means comprising a valve member fixed to the underside of the closed end of said hood, said standpipe opening being at the top thereof such that raising and lowering of said hood opens and closes said standpipe opening.

4. The apparatus of claim 3 in which said standpipe communicates through the floor of said reservoir with said transfusion means.

5. The apparatus of claim 2 including air vent means communicating from within the upper portion of said hood to the upper portion of said reservoir for venting said hood to the upper portion of said reservoir and for preventing draining of said reservoir to below the top of said standpipe.

6. A blood conservation system capable of receiving blood from a patient, the system comprising:
   a reservoir;
   means for releasably connecting said reservoir to a patient for receiving body liquids including blood from the patient;
   transfusion means for receiving blood from said reservoir; and
   means for transferring blood from said reservoir to said transfusion means and comprising valve means actuable for draining blood from said reservoir and including a valve stem extending through a wall of said reservoir adjacent the upper end of said reservoir, said reservoir having guide means for guiding said stem, and means actuable for moving said valve stem to open and close said valve means.

7. A blood conservation system capable of receiving blood from a patient, the system comprising:
   a reservoir;
   means for releasably connecting said reservoir to a patient for receiving body liquids including blood from the patient;
   transfusion means for receiving blood from said reservoir; and
   means for transferring blood from said reservoir to said transfusion means and comprising valve means actuable for draining blood from said reservoir and including a valve stem extending through a wall of said reservoir adjacent the upper end of said reservoir, said reservoir having guide means for guiding said stem, and means actuable for moving said valve stem to open and close said valve means, in which said means actuable for moving said valve stem comprise a manually actuable handle on the outside of said reservoir and connected to a part of said valve stem extending outside of said reservoir.

8. The apparatus of claim 7 in which said handle comprises an elongate member having an intermediate portion connected to said valve stem and means spaced from said valve stem and defining a fulcrum on which said handle is pivotable on said reservoir to open said valve means.

9. A blood conservation system capable of receiving blood from a patient, the system comprising:
   a reservoir;
   means for releasably connecting said reservoir to a patient for receiving body liquids including blood from the patient;
   transfusion means for receiving blood from said reservoir; and
   means for transferring blood from said reservoir to said transfusion means and comprising valve means actuable for draining blood from said reservoir and including a valve stem extending through a wall of said reservoir adjacent the upper end of said reservoir, said reservoir having guide means for guiding said stem, and means actuable for moving said valve stem to open and close said valve means, in which said valve stem is vertically reciprocable in said reservoir, said guide means comprising a vertical tubular member in which said valve stem is vertically slidable.

10. The apparatus of claim 9 in which said valve stem and guide means trap a compression spring therebetween, said spring being oriented to urge said stem to close said valve means.

11. The apparatus of claim 9 in which said valve stem is snugly slidable in a bore in said guide means, seal means distributed along said valve stem and bore, said reservoir having a suction passage connectable to a suction source, a suction port open to the interior of said reservoir, suction valve means between said suction passage and suction port, said suction valve means being defined by a portion of said stem and bore, such that raising said valve stem to open said valve means to drain blood from said reservoir also disconnects said suction passage from said suction port, vent valve means between the atmosphere outside said reservoir and said suction port, said vent valve means being defined by a further portion of said valve stem and guide such that raising said valve stem to open said valve means to drain blood from said reservoir also vents said reservoir to the outside atmosphere.

12. The apparatus of claim 11 in which said means for transferring blood comprises first valve means adjacent the bottom of said reservoir and openable to allow liquid to flow from said reservoir to said transfusion means;
second valve means interposed between a suction passage connectable to a suction source and a suction port in said reservoir, said second valve means having an open state for evacuating said reservoir to draw body fluids to a patient and a closed state for blocking communication between said reservoir and suction source;
third valve means for alternately closing and opening said reservoir to the surrounding atmosphere; and
valve actuator means operatively connected to said valve means and actuable for simultaneously opening said first and third valve means and closing said second valve means.

13. The apparatus of claim 1 including means for alternately connecting said reservoir to a suction source and to the atmosphere, such connecting means being independent of said means for connecting said patient to said reservoir, said alternately connecting means comprising a suction passage to said suction source and a vent passage to the atmosphere from said reservoir and valve means actuable for alternately opening communication of said suction passage and vent passage to said reservoir.

14. The apparatus of claim 13 including a float valve contactable by liquid in said reservoir which has risen to a relatively high level and interposed between said valve means and reservoir for blocking passage of said liquid to said suction and vent passages.

15. The apparatus of claim 13 including a hydrophobic filter means interposed between said reservoir and valve means for blocking entry of liquid in said reservoir into said suction passage and vent passage and sterilizing air drawn from said vent passage into said reservoir.

16. The apparatus of claim 13 including a hydrophobic filter means of pore size suitable for (1) preventing of entry of liquid into said suction passage and (2) sterilizing air drawn into said reservoir from the surrounding atmosphere, said valve means being located between said hydrophobic filter on the one hand and, on the other hand, said suction passage and vent passage to the atmosphere surrounding said reservoir.

17. The apparatus of claim 1 including a vacuum indicator visible on said reservoir for indicating visually the presence of absence of a sub-atmospheric pressure in said reservoir.

18. A system for transferring blood from a patient, comprising:
a reservoir;
means for releasably connecting said reservoir to a patient for receiving body fluids, including blood, from the patient;
a suction passage on said reservoir connectable to a suction source;
a vent passage on said reservoir connected to the atmosphere around said reservoir;
a blood outlet on said reservoir;
means for controlling the pressure in said reservoir, said valve means including a manually actuable valve means interposed between said suction passage and vent passage on the one hand and said reservoir on the other hand, said valve means being alternatively actuable for connecting said suction passage and vent passage alternately to said reservoir.

19. The apparatus of claim 18 in which said valve means includes a suction valve and a vent valve actuable with said suction valve for venting the reservoir to the atmosphere with the suction valve disconnecting said suction passage from said reservoir, said valve means further including an outlet valve actuable with said suction valve and vent valve for allowing blood to drain from said reservoir through said blood outlet with the suction valve disconnecting said suction passage from said reservoir and said vent valve venting said reservoir to the atmosphere.

20. The apparatus of claim 18 in which said valve means comprises a generally upstanding valve stem, a guide in said reservoir in which said stem is axially slidable, means outside said reservoir for shifting said stem along said guide between a blood receiving position and a blood outputting position, said stem in said blood receiving position having means connecting said suction passage to said reservoir to produce a sub-atmospheric pressure in said reservoir and therefore for sucking blood from the patient into said reservoir, said stem in said blood outputting position having means disconnecting said suction passage from said reservoir and instead venting the upper end of said reservoir to the outside atmosphere and connecting the lower end of said reservoir to a means for receiving blood from said reservoir.

21. The apparatus of claim 20 including a float valve and a hydrophobic filter interposed between said stem and reservoir for preventing liquid from said reservoir entering said suction passage, said hydrophobic filter being interposed between said vent and reservoir to sterilize air drawn into said reservoir from said vent.

22. The apparatus of claim 18 including a suction source comprising a portable base unit including a battery electric supply and a vacuum pump powered thereby.

* * * * *

UNITED STATES PATENT AND TRADEMARK OFFICE
CERTIFICATE OF CORRECTION

PATENT NO. : 4,994,022
DATED : February 19, 1991
INVENTOR(S) : Michael W. Steffler, et al It is certified that error appears in the above-identified patent and that said Letters Patent is hereby corrected as shown below:

```
Column 13, line 52; change "the" to ---said---.
Column 13, line 54; change "the" to ---said---.

Column 15, line 18; change "11" to ---1---.
Column 16, line 5;  change "of" (first occurrence)
                    to ---or---.
```

Signed and Sealed this

Second Day of March, 1993

*Attest:*

STEPHEN G. KUNIN

*Attesting Officer*      Acting Commissioner of Patents and Trademarks